US011536679B2

(12) United States Patent
Swett (10) Patent No.: US 11,536,679 B2
(45) Date of Patent: Dec. 27, 2022

(54) LEAF CELL SENSOR

(71) Applicant: Saudi Arabian Oil Company, Dhahran (SA)

(72) Inventor: Dwight W. Swett, Cypress, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 114 days.

(21) Appl. No.: 17/090,314

(22) Filed: Nov. 5, 2020

(65) Prior Publication Data
US 2021/0131990 A1    May 6, 2021

Related U.S. Application Data

(60) Provisional application No. 62/930,805, filed on Nov. 5, 2019.

(51) Int. Cl.
*G01N 27/12* (2006.01)
*E21B 49/08* (2006.01)
*G01N 33/28* (2006.01)

(52) U.S. Cl.
CPC ....... *G01N 27/125* (2013.01); *E21B 49/0875* (2020.05); *G01N 33/2823* (2013.01)

(58) Field of Classification Search
CPC .............. G01N 27/125; G01N 33/2823; E21B 49/0875; H01L 24/78
See application file for complete search history.

(56) References Cited

U.S. PATENT DOCUMENTS 4,240,285 A * 12/1980 Langdon ................ G01N 9/002
73/290 V 9,952,343 B2    4/2018 Swett
(Continued)

FOREIGN PATENT DOCUMENTS

WO    WO-2013/009932 A2    1/2013
WO    WO-2018/017558 A1    1/2018
(Continued)

OTHER PUBLICATIONS

Chaudhuri, A. et al., An Algorithm for Determining Volume Fractions in Two-Phase Liquid Flows by Measuring Sound Speed, Jrnl. Fluids Engin., 134:101301-1-7 (2012).
(Continued)

*Primary Examiner* — Catherine T. Rastovski
*Assistant Examiner* — Kaleria Knox
(74) *Attorney, Agent, or Firm* — Osha Bergman Watanabe & Burton LLP (57) ABSTRACT

This specification describes a leaf cell resonator sensor based on a geometry of Rhodonea conformal contours joined circumferentially in an eight-fold symmetry by central spoke electrode members. The resonator sensor may provide simultaneous and congruent measurement of fluid density and sound speed based on interaction of the leaf cell dynamics with self-formed Helmholtz cavity dilatational response of the fluid, and the associated changes in electrical admittance spectra in the sensor resulting from changes in fluid acoustic properties. A leaf cell resonator sensor may be capable of retrieving a density and sound speed measurement from fluid independent of the method of deployment, resulting from the principle of the self-formed Helmholtz resonant cavity feature that develops a standing acoustic wave pattern in the fluid without extraneous reflecting structure/hardware.

16 Claims, 7 Drawing Sheets

(56) References Cited

U.S. PATENT DOCUMENTS

| | | | |
|---|---|---|---|
| 10,054,707 B2 | 8/2018 | Swett | |
| 2002/0093348 A1* | 7/2002 | Buhler | H01L 24/78 |
| | | | 324/696 |
| 2008/0215245 A1 | 9/2008 | Reittinger | |
| 2014/0367092 A1* | 12/2014 | Roberson | E21B 47/005 |
| | | | 166/250.01 |
| 2016/0326866 A1* | 11/2016 | Swett | G01N 29/036 |
| 2018/0110913 A1* | 4/2018 | Loderer | A61M 39/281 |
| 2020/0041395 A1* | 2/2020 | Swett | G01N 9/002 |

FOREIGN PATENT DOCUMENTS

| | | | | |
|---|---|---|---|---|
| WO | WO-2018017558 A1 * | 1/2018 | | E21B 47/0005 |
| WO | WO-2020/027941 A1 | 2/2020 | | |
| WO | WO-2020/142530 A1 | 7/2020 | | |
| WO | WO-2021/090114 A1 | 5/2021 | | |

OTHER PUBLICATIONS

International Search Report for PCT/IB2020/060108, 6 pages (dated Feb. 19, 2021).

Meng, G. et al., Composition measurements of crude oil and process water emulsions using thick-film ultrasonic transducers, Chem. Engin. Process., 45:383-391 (2006).

Swett, D. W., Experimental Characterization of a Piezoelectric Leaf-Cell Sensor for Simultaneous Fluid Density and Sound Speed Measurement, IEEE Sens. Lett., 4(5):1-4 (2020).

Tsouris, C. and Tavlarides, L. L., Volume fraction measurements of water in oil by an ultrasonic technique, Ind. Eng. Chem. Res., 32(5):998-1002 (1993).

Written Opinion for PCT/IB2020/060108, 12 pages (dated Feb. 19, 2021).

\* cited by examiner

LEAF CELL SENSOR

RELATED APPLICATIONS

This application claims benefit of U.S. Provisional Patent Application No. 62/930,805, filed on Nov. 5, 2019, entitled "Leaf Cell Sensor," the disclosure of which is incorporated herein by reference in its entirety.

TECHNICAL FIELD

This specification describes example implementations of a tool for performing testing of fluids in a wellbore.

BACKGROUND

Generally, fluids in the petrochemical industry, for example, fluids in a wellbore of an oil field, may be single or multiphase fluids. Wellbore fluids may include mixtures of miscible and immiscible fluids, for example, mixtures of oil and water. Wellbore fluids may include mixtures of liquid and gas, liquid and solid, gas and solid, or mixtures of liquid, gas, and solid. Environmental conditions in a wellbore and in fluid systems associated with the extraction and transport of hydrocarbons may vary significantly. For example, temperatures in a wellbore may vary from approximately 2° C. to over 130° C. Pressures may vary from atmospheric pressure to over 50 Megapascals (MPa) at the bottom of an oil well. Composition of a wellbore fluid and environmental conditions in a wellbore greatly affect the rheological properties of a fluid. Analysis of rheological properties in situ may be important to ensure proper handling of fluids in a wellbore and related fluid systems. For example, if a wellbore fluid exhibits a viscosity above a certain threshold value, mitigating measures may need to be taken to maximize the degree of fluid extraction. Such measures include thermal methods (for example, hot fluid circulation), pressure management (for example, pumping or boosting), or chemical treatments. Because these measures may be costly, accurate determination of wellbore fluid properties is critical.

SUMMARY

This specification describes an example leaf cell resonator sensor based on a geometry of Rhodonea conformal contours joined circumferentially in an eight-fold symmetry by central spoke electrode members. An example leaf cell resonator sensor may utilize a self-formed Helmholtz acoustic cavity response of fluid circumferentially enclosed by the leaf cell resonator boundary. A leaf cell resonator sensor may provide simultaneous and congruent measurement of fluid density and sound speed based on interaction of the leaf cell dynamics with self-formed Helmholtz cavity dilatational response of the fluid, and the associated changes in electrical admittance spectra in the sensor resulting from changes in fluid acoustic properties. A leaf cell resonator sensor may be capable of retrieving a density and sound speed measurement from fluid independent of the method of deployment, resulting from the principle of the self-formed Helmholtz resonant cavity feature that develops a standing acoustic wave pattern in the fluid without extraneous reflecting structure/hardware.

An example apparatus for fluid measurement includes a leaf cell having one or more piezoelectric radial components connected to a circumferential component. The one or more radial components and the circumferential component have a distal face and a proximal face. The example apparatus includes a first electrode positioned on the distal face of at least one radial component. The example apparatus includes a second electrode positioned on the proximal face of the at least one radial component. The example apparatus includes a voltage source having a negative terminal and a positive terminal, the negative terminal being connected to the first electrode and the positive terminal being connected to the second electrode.

The circumferential component may have a shape based on contour segments of the canonical Rhodonea conformal mapping geometry. The example apparatus may include an electric current measurement device connected to the first and second electrode to measure current flowing between the first and second electrode.

The example apparatus may include a processor of a computing device and a non-transitory computer readable medium storing instructions thereon, wherein the instructions, when executed, cause the processor to determine, from the measured current, one or more properties of the fluid. The one or more properties of the fluid may include fluid density or fluid sound speed. Determining may include determining electrical admittance spectra.

The fluid density (rho) may be determined at least in part based on the equation rho=(DR−DPHBW)+$\alpha_2$(DI2−DPHBW)+$\alpha_3\sqrt{DM2}$ where DR denotes a peak shift in a real part of complex admittance between air and fluid, DPHBW denotes change in bandwidth between air and fluid, DI2 denotes the valley shift in the imaginary part of admittance between air and fluid, and DM2 denotes the valley shift in admittance magnitude between air and fluid. The fluid sound speed (ss) may be determined at least in part based on the equation ss=$\alpha_1$DPH+$\alpha_2$ (DR−DPHBW)+$\alpha_3\sqrt{DI2-DPHBW}$ where DPH denotes a difference in phase peak of admittance between air and fluid, DR denotes a peak shift in the real part of admittance between air and fluid. DPHBW denotes change in bandwidth between air and fluid, and DI2 denotes the valley shift in the imaginary part of admittance between air and fluid.

The leaf cell may include eight radial components. The leaf cell may include lead zirconate titanate. The circumferential component may have an outer diameter of between 8 mm and 12 mm. The apparatus may be integrated into a production logging tool or a logging while drilling tool.

An example method for measuring one or more properties of a fluid includes immersing an apparatus into a volume of the fluid, where the apparatus includes a leaf cell having one or more piezoelectric radial components connected to a circumferential component. The example method includes applying a sinusoidal voltage across a first electrode and a second electrode, thereby inducing a sinusoidal strain in the piezoelectric radial component. The example method includes measuring a current flowing between the first electrode and the second electrode. The example method includes determining, from the current, the one or more fluid properties of the fluid.

The one or more properties of the fluid may include fluid density or fluid sound speed. The determining step may include determining electrical admittance spectra. The example method may include one or more reference measurements in air.

The example method may include determining fluid density (rho) at least in part based on the equation rho=$\alpha_1$ (DR−DPHBW)+$\alpha_2$(DI2−DPHBW)+$\alpha_3\sqrt{DM2}$, where DR denotes a peak shift in a real part of complex admittance between air and fluid, DPHBW denotes change in bandwidth between air and fluid, DI2 denotes the valley shift in the imaginary part of admittance between air and fluid, and DM2 denotes the valley shift in admittance magnitude between air and fluid.

The example method may include determining fluid sound speed (ss) at least in part based on the equation $ss = \alpha_1 DPH + \alpha_2 (DR - DPHBW) + \alpha_3 \sqrt{DI2 - DPHBW}$, where DPH denotes a difference in phase peak of admittance between air and fluid, DR denotes a peak shift in the real part of admittance between air and fluid. DPHBW denotes change in bandwidth between air and fluid, and DI2 denotes the valley shift in the imaginary part of admittance between air and fluid.

The example apparatus or example methods may be used with a multiphase fluid. the example apparatus or example methods may be used with a wellbore fluid.

Any two or more of the features described in this specification, including in this summary section, may be combined to form implementations not specifically described in this specification.

All or parts of the methods, systems, and techniques described in this specification may be implemented as a computer program product. The computer program product may include instructions that are stored on one or more non-transitory machine-readable storage media. The instructions may be executable on more or more processing devices.

The details of one or more implementations are set forth in the accompanying drawings and the description. Other features and advantages will be apparent from the description and drawings, and from the claims.

DETAILED DESCRIPTION

Measurement of one or more rheological properties of a fluid may allow determination of other properties, for example, the composition of the fluid. Acoustic measurements can be used for determining composition and chemical properties of unknown fluids, for example, multi-phase fluids, and may be applied to fluid identification (ID) problems in a variety of sensor development fields. Without wishing to be bound by theory, certain chemometric correlations may exist between downhole multi-phase fluid properties and bulk fluid acoustic properties, for example, of sound speed and density. Example downhole multi-phase fluid properties include volume fractions, gas-oil-ratio (GOR), American Petroleum Institute oil gravity (API) (where API gravity=141.5/SG−131.5, where SG is the specific gravity of crude oil), live-oil density, and live-oil compressibility. This specification describes an example resonant cell geometry sensor that provides real-time bulk fluid acoustic properties measurements that may be part of a system and methods for multi-phase fluid decomposition analysis.

To measure rheological properties of a fluid, for example, wellbore fluid, two separate sensors may be deployed at different locations to acquire two measurements comprising, for example, fluid density and sound speed. Measurement algorithms for some single-mode sound speed sensors may be applied that estimate multi-phase fluid properties, such as volume fraction of continuous and dispersed phases. These algorithms, however, rely on a priori knowledge of the mass density of both the continuous and dispersed phase of a fluid flow as inputs to the estimation. Due to the constraints of this a priori density property requirement, these single-mode sensors may be used primarily for surface systems that are used in the oil and gas industry where these types of data are readily available. These types of sensor approaches may not applicable to in-situ downhole fluid identification applications. Analysis of multi-phase fluid composition may require a simultaneous and congruent measurement of two (or more) fluid properties, that is, at the same instant and from the same identical set of particles comprising the fluid domain. Example sensors described in this specification may retrieve fluid property measurements, for example, of both continuous and dispersed phase, simultaneously and congruently, forming a basis for in situ and real-time multi-phase compositional analysis.

An example resonator sensor as described in this specification may provide simultaneous and congruent measurement of acoustic properties that may allow in situ downhole discrimination of bulk fluid properties, for example, mass density and sound speed. An example fluid may be a multi-phase fluid. An example fluid may include oil, water, gas, drilling fluid, or a combination of two or more of oil, water, gas, and drilling fluid. An example resonator sensor implementation may use the dynamic acoustic behavior of a dilatational fluid volume brought into resonance by electro-mechanical means to form an algorithm that relates feedback coupling between the resonating fluid volume and the electromechanical device to infer acoustic properties of the fluid. The dilatational resonance of the fluid volume may be formed intrinsically by curvilinear Rhodonea contours of a leaf-type cell piezoelectric structure acting on a subdomain of a fluid that flows through the cell structure to create an intrinsic Helmholtz cavity response, for example, using only the leaf cell and the fluid.

Figure 1:
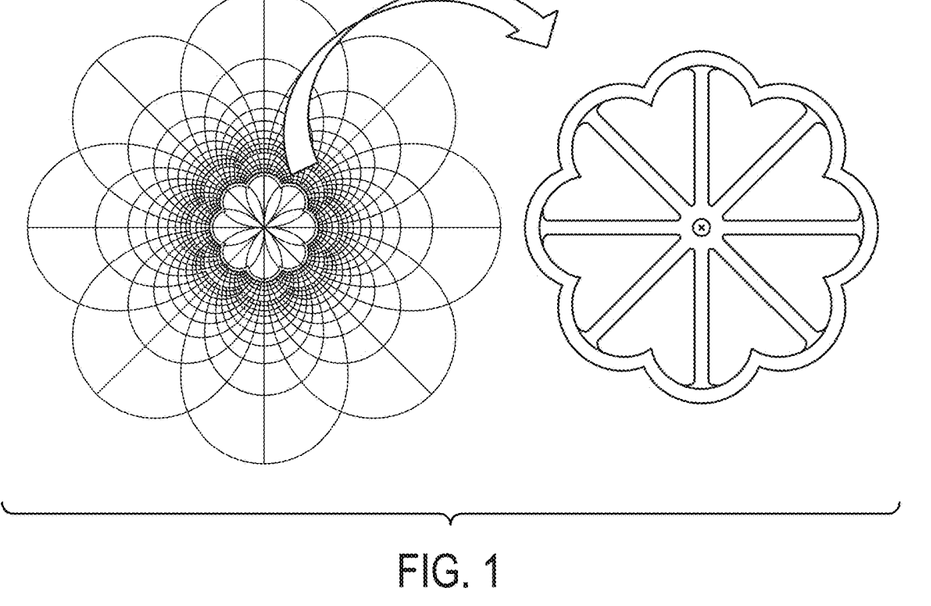
FIG. 1 shows a graphical representation of a Rhodonea cell resonator geometry based on conformal mapping contours.

FIG. 1 shows a graphical representation of an example Rhodonea cell resonator geometry based on conformal mapping contours. The geometry for an example leaf cell resonator element may be based on contour segments of the canonical Rhodonea conformal mapping geometry defined by the mathematical relations:

$$x = \pm \frac{1}{\rho}\sqrt{\rho + u} \qquad \text{Eq. (1)}$$

$$y = \pm \frac{1}{\rho}\sqrt{\rho - u} \qquad \text{Eq. (2)}$$

$$\rho = \sqrt{u^2 + v^2} \qquad \text{Eq. (3)}$$

Where 'u' and 'v' are the are the Rhodonea conformal domain coordinates as illustrated in the constant coordinate 'x'/'y' plot of FIG. 1, and ρ designates a variable function of the two mapping variables 'u' and 'v'. The conformal contour segments form an eight-fold symmetry in the leaf cell resonator geometry and are joined by eight central spoke members.

Figure 2:
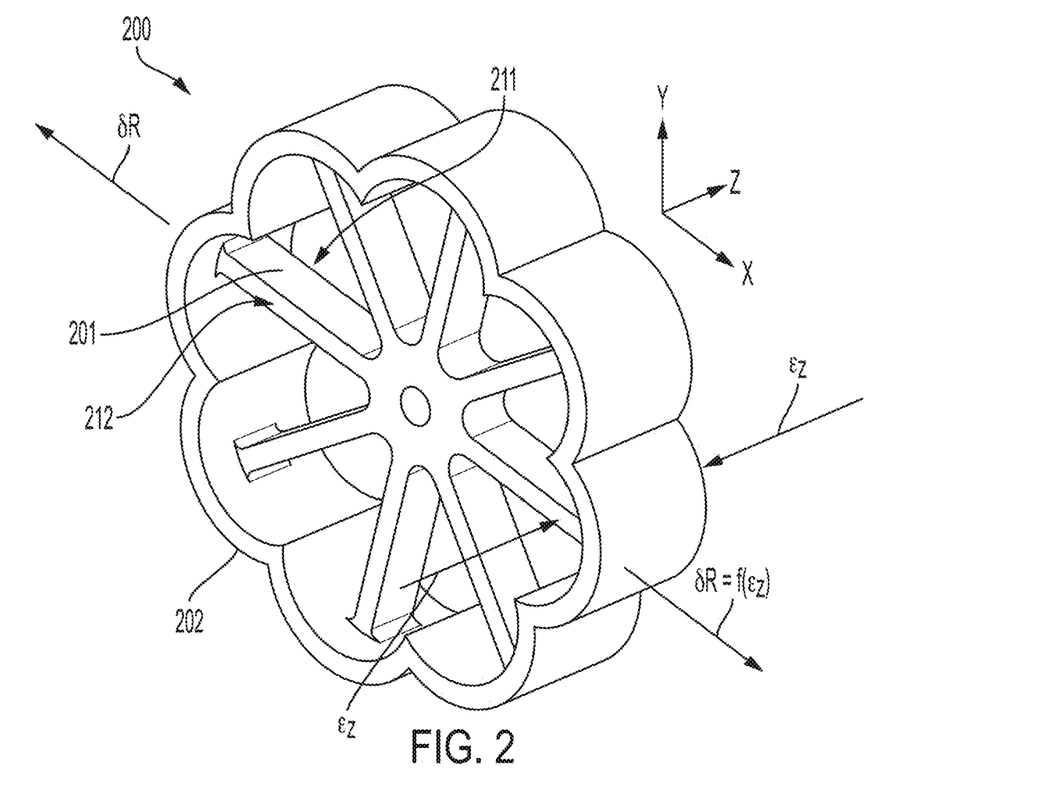
FIG. 2 is a perspective view of an example leaf cell.

An example leaf cell 200 is shown in FIG. 2. In some implementations, a leaf resonator is excited by applying an electrical voltage potential across electrically conductive electrode surfaces placed on the top and bottom faces (for example, proximal face 211 and distal face 212) of one or more central spoke members 201 as illustrated in FIG. 2. The applied voltage creates a through-thickness mechanical strain (strain along the Z-axis, $\varepsilon_z$) in each spoke member due to the piezoelectricity of the leaf cell material. As a consequence of the Poisson's ratio effect (the negative of the ratio of transverse strain to axial strain), this through-thickness strain creates a corresponding longitudinal strain in each spoke member 201 in the radial direction (X-Y plane, δR) that results in symmetrical dilatation of the leaf cell resonator 202. Resonance excitation may therefore be developed by applying a harmonic electrical potential that creates a frequency response in the cell in which the eight curvilinear segments fold and unfold energetically to perform work on the fluid captured within the eight-fold contour boundary. In some implementations, a leaf cell may include 1, 2, 3, 4, 5, 6, 7, 8, 9, or 10 curvilinear segments. The instantaneous acoustic impedance of the fluid within the cell boundary may then detected as a change in the stress field within the piezoelectric spoke members as evidenced, for example, as a change in the electrical current in the leaf cell electrodes and the integrated electrical circuit. The fluid properties may then be characterized, for example, by an instantaneous electrical admittance spectrum where changes in certain parameters of the admittance spectrum (for example, frequency, bandwidth, and shape) form the basis for a fluid identification measurement algorithm.

Electrical admittance is a measure of how easily a circuit or device will allow a current to flow and is defined as admittance Y=1/Z, where Z is the impedance. In reactive (alternating current) circuits, voltage V=IZ, where V and I are the complex scalars in the voltage and current respectively, and Z is the complex impedance. In Cartesian form, impedance is defined as Z=R+jX where the real part of impedance is the resistance R and the imaginary part is the reactance X (the opposition of a circuit element to a change in current or voltage). The mechanical deformation of a conductor (for example, a leaf cell) alters the resistance and reactance of the conductor, and a change in current (for example, phase shift or magnitude) flowing across the conductor may be detected and used to determine complex admittance spectra.

Figure 3A:
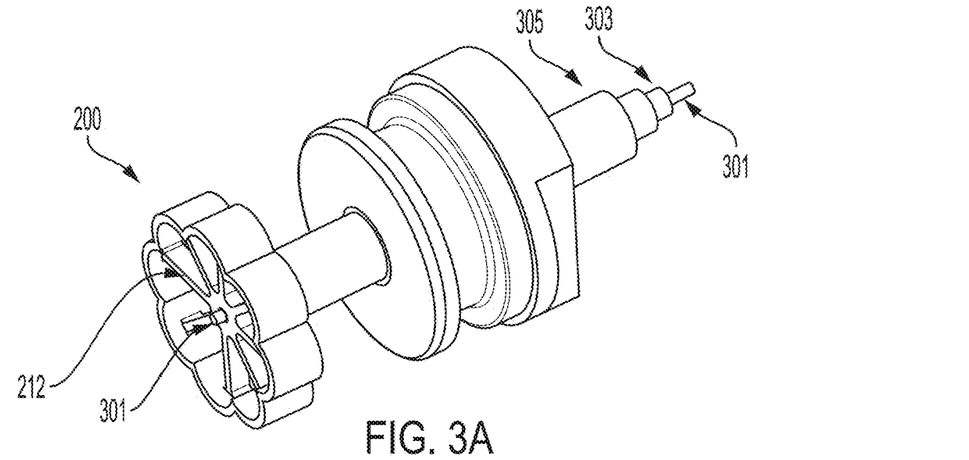
FIG. 3A is a perspective view of an example leaf cell sensor assembly.
Figure 3B:
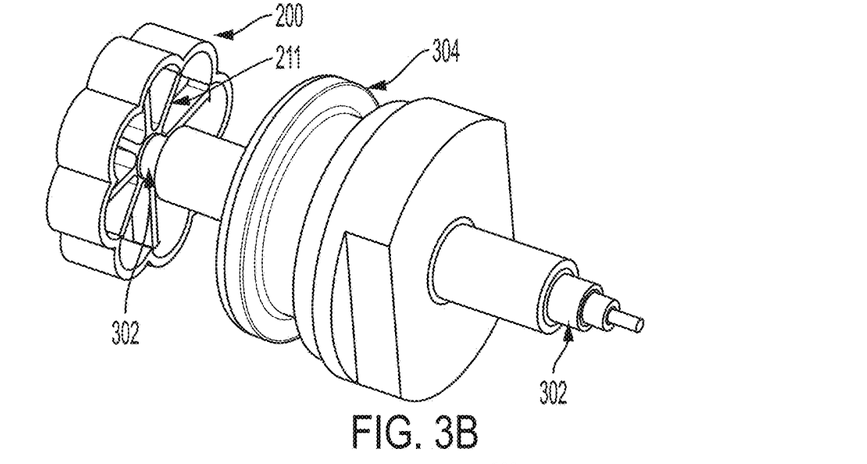
FIG. 3B is another perspective view of an example leaf cell sensor assembly.
Figure 4A:
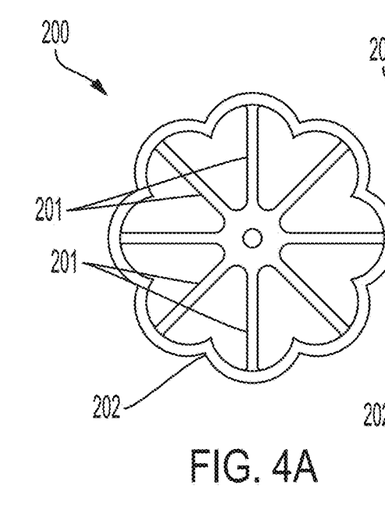
FIG. 4A shows a frontal view of an example leaf cell.
Figure 4B:
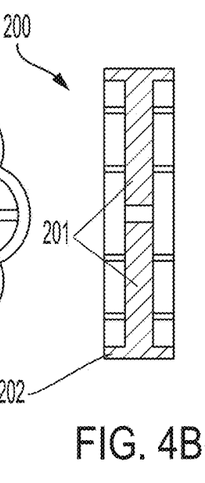
FIG. 4B shows a cut-away side view of an example leaf cell.
Figure 4C:
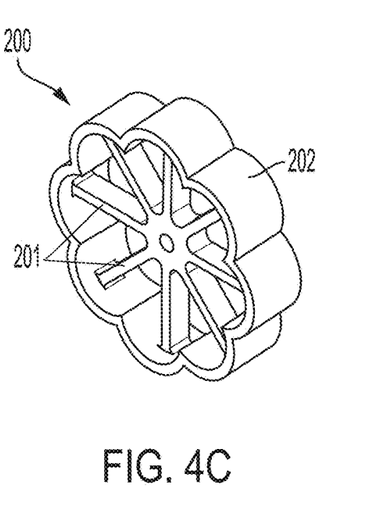
FIG. 4C shows a perspective view of an example leaf cell.

An example leaf cell sensor assembly design is illustrated in FIG. 3A and FIG. 3B. The design concept is based on a coaxial electrical feedthrough approach. An example sensor assembly 300 includes an example leaf cell 200 at a distal end of the assembly. An example leaf cell 200 may include one or more radial components (spokes) and a circumferential component (resonator) having a shape based on contour segments of the canonical Rhodonea conformal mapping geometry defined, for example, by the mathematical relations shown in FIG. 1. FIG. 4A shows a frontal view of an example leaf cell 200. FIG. 4B shows a cut-away side view of an example leaf cell 200. FIG. 4C shows a perspective view of an example leaf cell 200. In some implementations, an outer diameter of a resonator is between 100 millimeter and 5 millimeter (mm). In some implementations, an outer diameter of a resonator is between 8 mm and 12 mm. In an example implementation, an outer diameter of a resonator is 10 mm. A leaf cell may include two or more electrodes that may be connected to an inner contact and an outer contact, respectively, for example, of a pressure feedthrough. In some implementation, an electrode may be placed on a spoke of the leaf cell. For example, an inner contact 301 may be connected to an electrode on a distal face 212 of a leaf cell 200, and an outer contact 302 may be connected to an electrode on a proximal face 211 of the leaf cell 200. In some implementations, example pressure feedthrough contacts may include one or more conducting elements that run along a length of a feedthrough assembly. An example inner contact 301 and an example outer contact 302 are otherwise insulated from each other, for example, by an inner insulator 303, such that current flows between the electrodes. Outer contact 302 may be insulated from one or more components (for example, a feedthrough housing 304) of the leaf cell sensor assembly 300 by outer insulator 305. Inner contact 301 and outer contact 302 of the example pressure feedthrough may be connected to a voltage source. In some implementations, an inner contact may be connected to a negative terminal of the voltage source, and an outer contact may be connected to a positive terminal of the voltage source. In some implementations, an inner contact may be connected to a positive terminal of the voltage source, and an outer contact may be connected to a negative terminal of the voltage source. Electrodes and contacts may be connected to a leaf cell such that a voltage can be applied across the thickness of the leaf cell spokes, for example, spokes 201. An inner contact and an outer contact may be connected to an electric current measurement device, for example, an ammeter, to measure current across the thickness of a leaf cell, for example, leaf cell 200.

In some implementations, one or more components of a leaf cell sensor may be adapted to a variety of downhole fluid identification applications including production logging, logging while drilling, and formation sampling and testing. A leaf cell sensor may be implemented as a stand-alone device or may be integrated into one or more downhole tools, for example, production logging or logging while drilling tools.

An example leaf cell sensor operates on the principle that upon excitation of the leaf cell a nearly uniform cylindrical shaped pressure distribution is developed throughout an interior fluid region encompassed by the leaf cell boundary, where the pressure distribution is that of a classical Helmholtz resonator cavity response, but without the reflective walls of a cavity. This aspect of the resonance response is an intent of design for the sensor to interact specifically with the bulk modulus of a fluid medium, and subsequently provide sensitivity to changes in the fluid properties, for example, density and sound speed, from, for example, the compressibility of the fluid. As a result, a unique feature of the leaf cell resonator sensor is that the sensor is capable of retrieving fluid measurements, for example, a density or sound speed measurement, or both, from the fluid independent of the method of deployment, as there is no need for extraneous boundaries in order to develop the Helmholtz cavity-type response. In effect, the resonance characteristics of the fluid volume are coupled intrinsically to the dynamics of the set of curvilinear Rhodonea contour arcs and spoke members comprising the leaf-type cell piezoelectric structure, for example, through the dynamic compressibility of the fluid.

Figure 5:
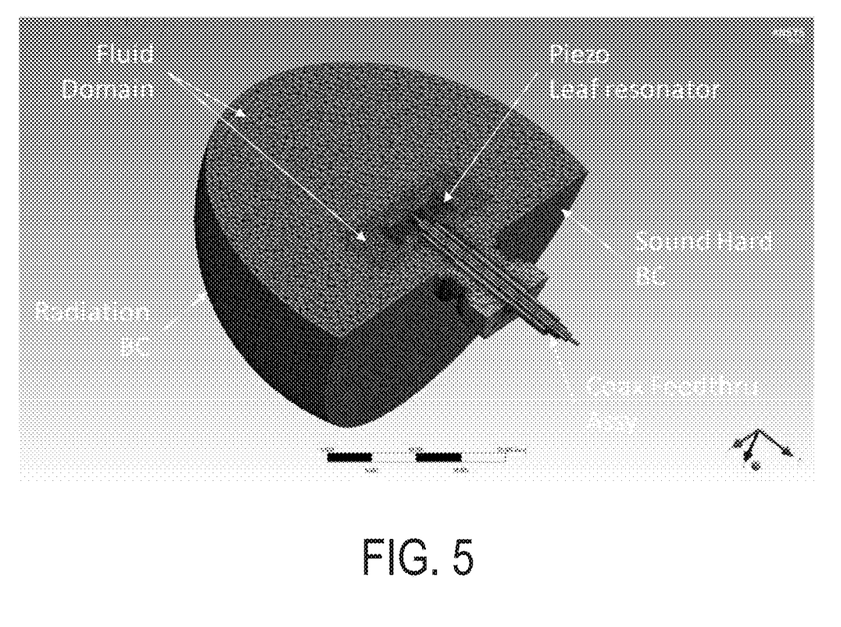
FIG. 5 is a cut-away perspective view of an example finite element model for multiphysics simulations of an example leaf cell resonator.

In an example design process for developing a conceptual leaf cell sensor assembly, design trade studies were conducted in the form of a series of Multiphysics harmonic simulations using a commercial finite element software package (Ansys®). The analyses used a coupled piezoelectric-structural-acoustic finite element model that includes detailed representations for an example lead zirconate titanate (PZT) leaf cell, the coaxial feedthrough structures, and the acoustic fluid domain. Other materials that may be used for a leaf cell include crystalline materials (for example, Langasite, Gallium orthophosphate, Lithium niobate, Lithium tantalite, Quartz, Berlinite, Rochelle salt, or Topaz), ceramics (for example, potassium niobate, sodium tungstate, zinc oxide, sodium potassium niobate, Bismuth ferrite, Sodium niobate, Barium titanate, Bismuth titanate, or Sodium bismuth titanate), or polymers (for example, Polyvinylidene Chloride). The model included appropriate fluid-structural interaction and non-reflecting radiation conditions on the fluid boundary to represent placing the sensor assembly in an open-field type fluid environment. The example finite element model utilized in the simulations is illustrated in FIG. 5 with the corresponding fluid acoustic boundary conditions (BC) highlighted.

Figure 6:
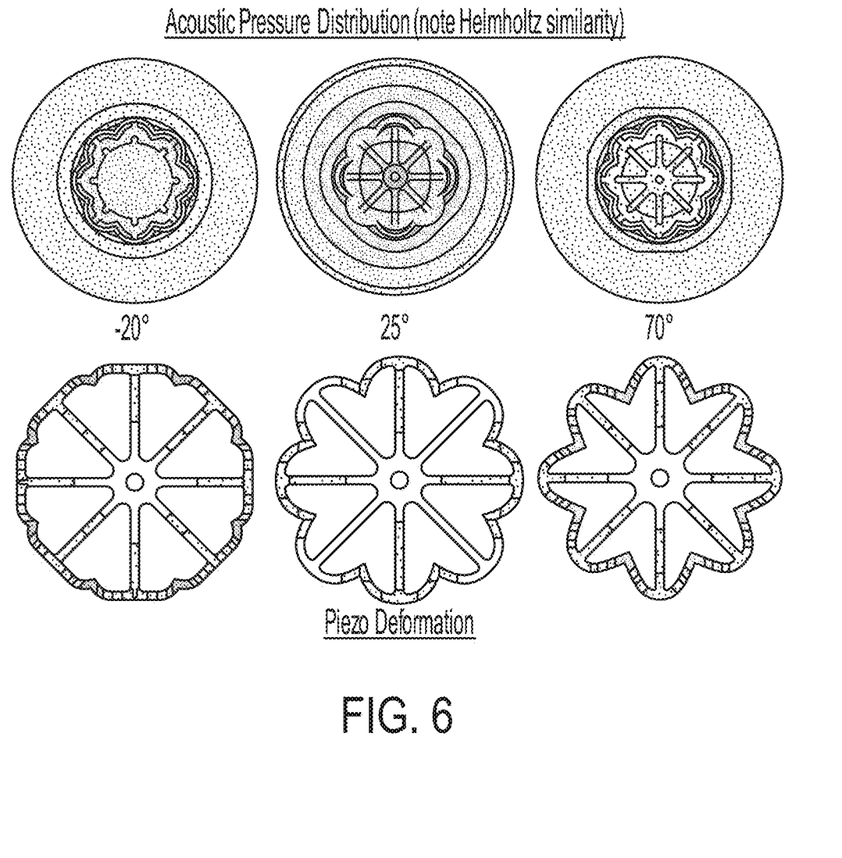
FIG. 6 is a graphical representation of resonance frequency response in a pure water fluid domain at 47.35 kiloHertz (kHz).

Example simulation results for a frequency response to sinusoidal excitation by a leaf cell resonator in a pure water fluid domain are shown in FIG. 6. For insight into the acoustic resonance response characteristics of the leaf cell resonator, a discrete frame comparison of sinusoidal cell deformation (FIG. 6, bottom) and the corresponding acoustic pressure distribution within the fluid (FIG. 6, top) was performed for the resonance frequency in pure water, which occurs at 47.35 kiloHertz (kHz). A feature of importance that can be identified from this typical response is the nearly uniform cylindrical shaped pressure distribution throughout the interior fluid region encompassed by the leaf cell boundary. This type of pressure distribution is typical of those developed in a classical Helmholtz resonator cavity in which the cavity is defined by a walled reflective volume, as opposed to the case here having no extraneous reflecting surfaces. This aspect of the resonance response is an intent of design for the sensor to interact specifically with the bulk modulus of the fluid medium, and thereby create sensitivity to changes in the fluid density and sound speed properties from the compressibility of the fluid. As a result, a unique feature of the leaf cell resonator sensor is that the sensor is capable of retrieving, for example, a sound speed measurement from the fluid, independent of the method of deployment because no extraneous cavity geometry is required to develop a Helmholtz cavity type response.

Figure 7:
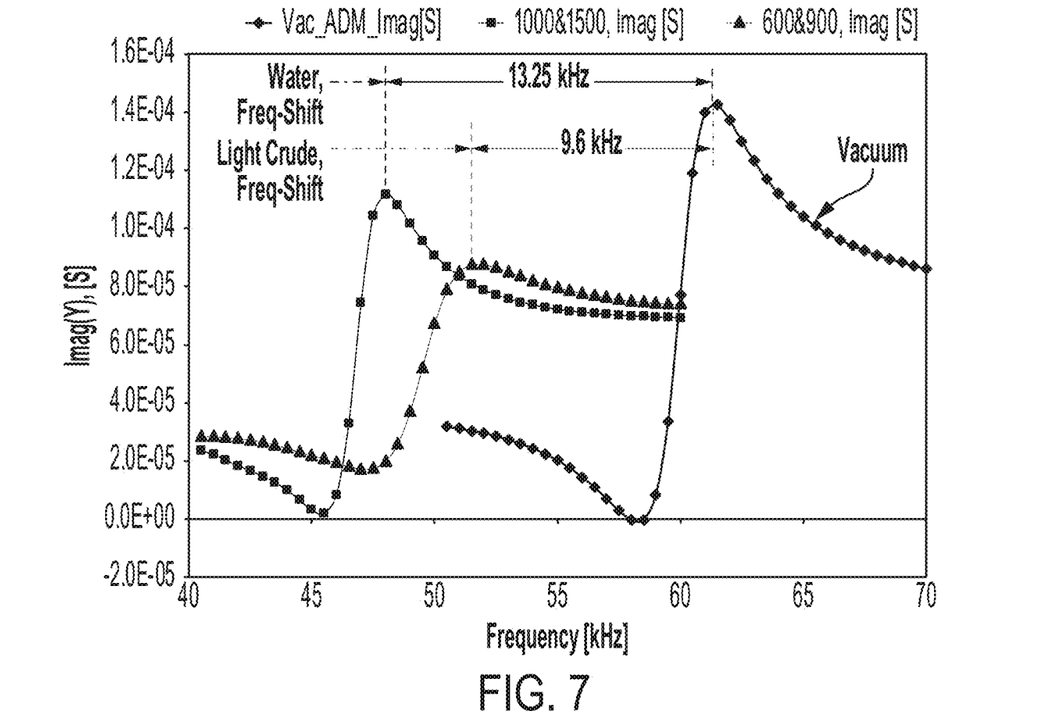
FIG. 7 shows example leaf cell sensor sensitivity to changes in fluid density: resonance frequency shift between vacuum and pure water, and resonance frequency shift between vacuum and light crude oil.
Figure 8:
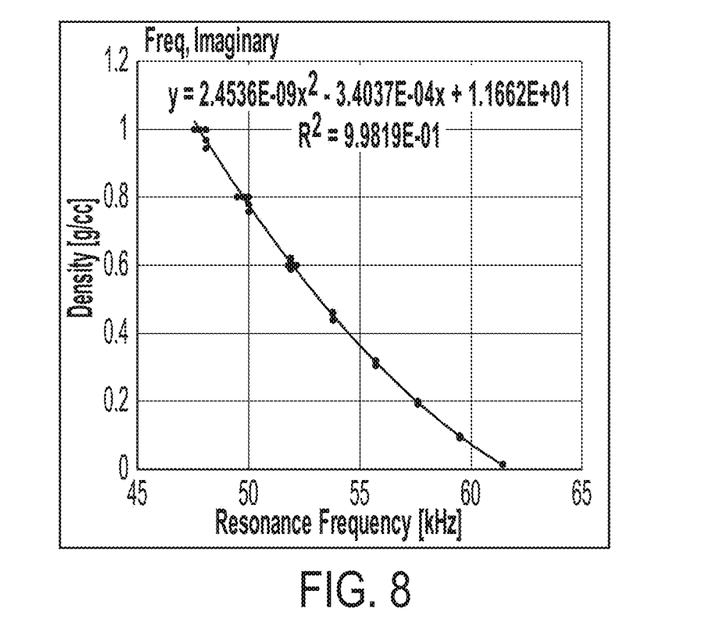
FIG. 8 shows parametric trends in resonance frequency with changes in fluid density of an imaginary component of electrical admittance in an example leaf cell sensor.

The sensitivity of an example leaf cell resonator sensor to changes in fluid acoustic properties may be illustrated in the electrical admittance frequency response spectra, for example, as shown in FIG. 7. Summarized here are the frequency response spectra of the imaginary component of the electrical admittance for a reference case of pure vacuum, in comparison with values obtained in pure water and a light crude oil. The resonance frequency of the example leaf cell resonator in a vacuum environment is 61.4 kHz. With the introduction of pure water (density $\rho=1$ grams/cubic centimeter (g/cc)) surrounding the sensor, the resonance frequency shifts down to 48.1 kHz, that is a change of 13.34 kHz/(g/cc). Replacement of pure water surrounding the sensor with a light crude oil (density $\rho=0.6$ g/cc) results in a resonance frequency change to 51.8 kHz. A more extensive set of parametric trends is illustrated in FIG. 8, which shows the change in resonance frequency of the imaginary component of admittance in a broad range of change in fluid density. The trends of the resonance frequency in FIG. 8 indicate a well-behaved correlation between the sensor admittance spectrum resonance frequency and the fluid density characterized by a simple second order fit for density ranging from ambient air to pure water.

Though the correlation indicated in FIG. 8 is compelling, a nonlinear mathematical algorithm for fluid properties measurement may not be desired from a practical viewpoint. Laboratory calibration is, by definition, limited to commercial fluid samples with traceable material properties over temperature. These commercial fluids are typically limited to a density range from 0.65 g/cc to no more than 0.90 g/cc. Consequently, in order to utilize a sensor in field environments involving typical downhole fluids that may range from 0.1 g/cc to 1.4 g/cc, a mathematical algorithm involving no more than linear dependencies may be highly desirable. From that perspective, an extended set of available parametric functions was considered to involve more variables associated with the sensor admittance response. A basic set of parametric functions may be built from seven admittance resonance frequency shifts: DI1 denotes the frequency shift of the peak of the admittance spectrum imaginary part from air to fluid. DI2 denotes the frequency shift of the valley of the admittance spectrum imaginary part from air to fluid. DR denotes the frequency shift of the peak of the admittance spectrum real part from air to fluid. DM1 denoted the frequency shift of the peak of the admittance spectrum magnitude from air to fluid. DM2 denotes the frequency shift of the valley of the admittance spectrum magnitude from air to fluid. DPH denotes the frequency shift of the peak of the admittance spectrum phase from air to fluid. DPHBW denotes the change of the bandwidth of the admittance spectrum phase from air to fluid.

Figure 9:
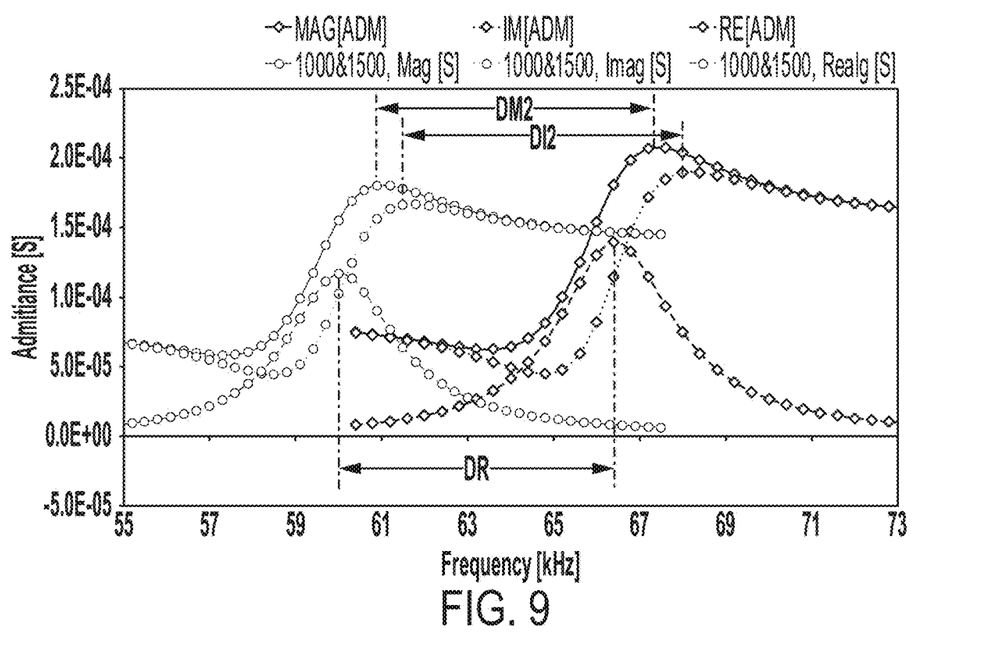
FIG. 9 shows example fluid identification (ID) parameters derived from sensor admittance amplitude spectra.
Figure 10:
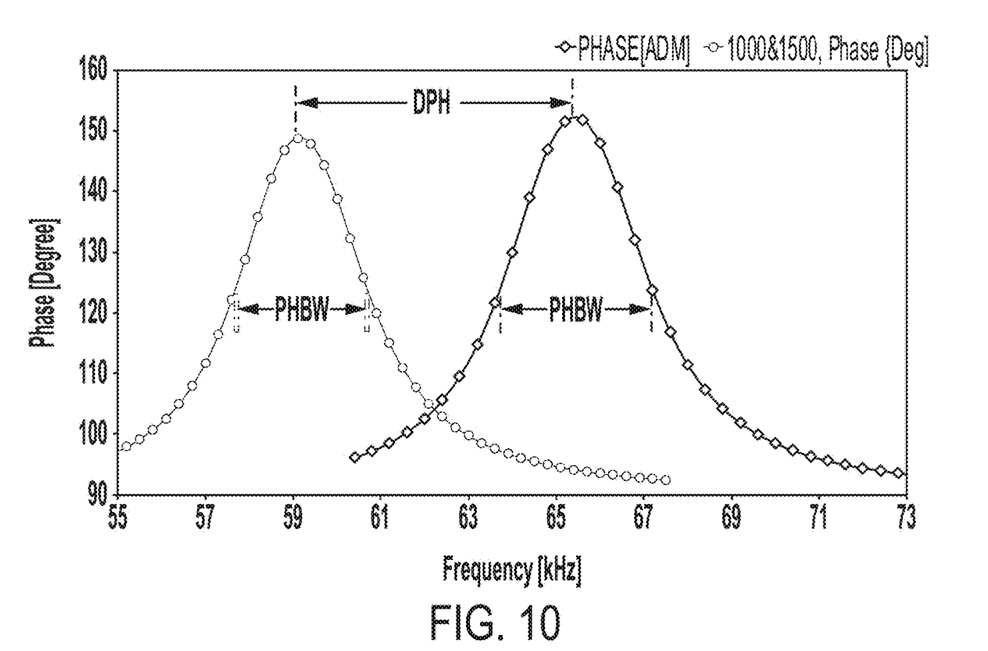
FIG. 10 shows example fluid ID parameters derived from sensor admittance phase spectra.

Example sensor admittance amplitude spectra are shown in FIG. 9. Example sensor admittance phase spectra are shown in FIG. 10. Spectra are shown for air and an example fluid (water) with a density of 1000 mg/cc (1 g/cc) and a sound speed of 1500 m/s.

Figure 11:
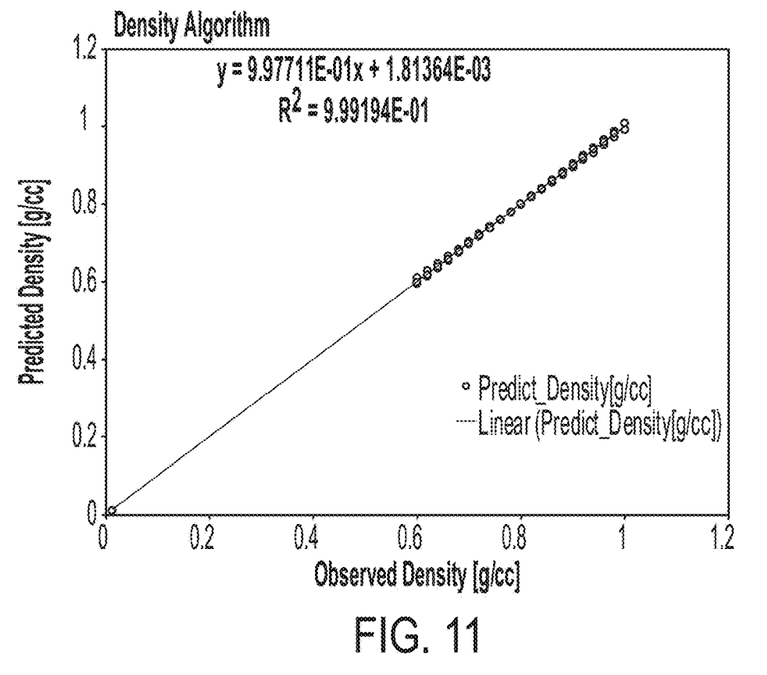
FIG. 11 shows a statistical plot of predicted density values obtained using an example algorithm as described in this specification vs. observed experimental results.

Using these seven basic parametric functions and unique differences of pairs, a statistical variable set of twenty eight parametric functions was constructed upon which to investigate fluid identification algorithm construction. This set of twenty eight parametric functions was implemented into a statistical (linear) multi-regression analysis using the MatLab® software package. The results of the multi-regression analyses for fluid density identification are shown in Table 1 and FIG. 11 for a range of fluid properties associated with sixty four different density/sound-speed combinations shown in Table 2.

TABLE 1

Max. Error = 0.01102 g/cc
Avg. Error = 0.00316 g/cc
Density R^2 = 0.99921

| rho_function | rho_coeff | t_test | p_test |
|---|---|---|---|
| "(DR − DPHBW)" | 3.439773034154E−04 | 1.501340048345E+02 | 6.992535937213E−83 |
| "(DI2 − DPHBW)" | −2.181813501313E−04 | −1.054567789273E+02 | 4.195763118402E−73 |
| "(DM2)^1/2" | −5.676581632404E−03 | −2.743745352172E+03 | 1.330346301263E−163 |

$$rho = \alpha_1(DR - DPHBW) + \alpha_2(DI2 - DPHBW) + \alpha_3\sqrt{DM2}$$

TABLE 2

| Sound Speed (m/s) | Density (g/cc) | Predict Density (g/cc) | Error (g/cc) |
|---|---|---|---|
| 323.2 | 0.01278 | 0.0128 | 0 |
| 1500 | 0.6 | 0.611 | 0.011 |
| 1500 | 0.62 | 0.6295 | 0.0095 |
| 1500 | 0.64 | 0.6481 | 0.0081 |
| 1500 | 0.66 | 0.6667 | 0.0067 |
| 1500 | 0.68 | 0.6853 | 0.0053 |
| 1500 | 0.7 | 0.7041 | 0.0041 |
| 1500 | 0.72 | 0.7229 | 0.0029 |
| 1500 | 0.74 | 0.7417 | 0.0017 |
| 1500 | 0.76 | 0.7606 | 0.0006 |
| 1500 | 0.78 | 0.7795 | 0.0005 |
| 1500 | 0.8 | 0.7985 | 0.0015 |
| 1500 | 0.82 | 0.8176 | 0.0024 |
| 1500 | 0.84 | 0.8366 | 0.0034 |
| 1500 | 0.86 | 0.8558 | 0.0042 |
| 1500 | 0.88 | 0.8749 | 0.0051 |
| 1500 | 0.9 | 0.8942 | 0.0058 |
| 1500 | 0.92 | 0.9134 | 0.0066 |
| 1500 | 0.94 | 0.9327 | 0.0073 |
| 1500 | 0.96 | 0.9521 | 0.0079 |
| 1500 | 0.98 | 0.9715 | 0.0085 |
| 1500 | 1 | 0.9909 | 0.0091 |
| 1200 | 0.6 | 0.5951 | 0.0049 |
| 1200 | 0.62 | 0.6154 | 0.0046 |
| 1200 | 0.64 | 0.6358 | 0.0042 |
| 1200 | 0.66 | 0.6562 | 0.0038 |
| 1200 | 0.68 | 0.6767 | 0.0033 |
| 1200 | 0.7 | 0.6972 | 0.0028 |
| 1200 | 0.72 | 0.7177 | 0.0023 |
| 1200 | 0.74 | 0.7383 | 0.0017 |
| 1200 | 0.76 | 0.7589 | 0.0011 |
| 1200 | 0.78 | 0.7795 | 0.0005 |
| 1200 | 0.8 | 0.8002 | 0.0002 |
| 1200 | 0.82 | 0.821 | 0.001 |
| 1200 | 0.84 | 0.8417 | 0.0017 |
| 1200 | 0.86 | 0.8625 | 0.0025 |
| 1200 | 0.88 | 0.8834 | 0.0034 |
| 1200 | 0.9 | 0.9042 | 0.0042 |
| 1200 | 0.92 | 0.9251 | 0.0051 |
| 1200 | 0.94 | 0.9461 | 0.0061 |
| 1200 | 0.96 | 0.967 | 0.007 |
| 1200 | 0.98 | 0.988 | 0.008 |
| 1200 | 1 | 1.0091 | 0.0091 |
| 900 | 0.6 | 0.5995 | 0.0005 |
| 900 | 0.62 | 0.6194 | 0.0006 |
| 900 | 0.64 | 0.6393 | 0.0007 |
| 900 | 0.66 | 0.6593 | 0.0007 |
| 900 | 0.68 | 0.6793 | 0.0007 |
| 900 | 0.7 | 0.6992 | 0.0008 |
| 900 | 0.72 | 0.7192 | 0.0008 |
| 900 | 0.74 | 0.7393 | 0.0007 |
| 900 | 0.76 | 0.7593 | 0.0007 |
| 900 | 0.78 | 0.7794 | 0.0006 |
| 900 | 0.8 | 0.7995 | 0.0005 |
| 900 | 0.82 | 0.8196 | 0.0004 |
| 900 | 0.84 | 0.8397 | 0.0003 |
| 900 | 0.86 | 0.8598 | 0.0002 |
| 900 | 0.88 | 0.88 | 0 |
| 900 | 0.9 | 0.9001 | 0.0001 |
| 900 | 0.92 | 0.9203 | 0.0003 |
| 900 | 0.94 | 0.9406 | 0.0006 |
| 900 | 0.96 | 0.9608 | 0.0008 |
| 900 | 0.98 | 0.981 | 0.001 |
| 900 | 1 | 1.0013 | 0.0013 |

The maximum value of the 'p-test' coefficients was p_test<<0.05, which indicated that the calculated model is highly relevant to the underlying physics and not simply a numerical artifact of the data set. This linear model was based on three parametric functions involving resonance frequency shifts as well as distortion due to change in the resonance bandwidth:

$$rho = \alpha_1(DR-DPHBW) + \alpha_2(DI2-DPHBW) + \alpha_3\sqrt{DM2}$$

where DR denotes peak shift in the real part of complex admittance between air and fluid, DPHBW denotes change in bandwidth between air and fluid, DI2 denotes the valley shift in the imaginary part of admittance between air and fluid, and DM2 denotes the valley shift in admittance magnitude between air and fluid. The maximum calculated density error over the range of sixty four fluid properties sets was 0.011 g/cc.

Figure 12:
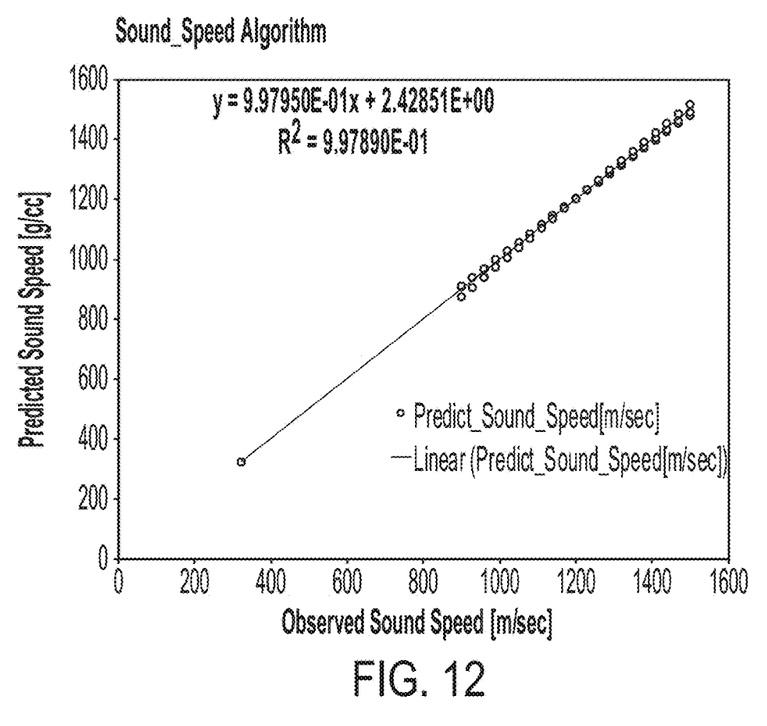
FIG. 12 shows a statistical plot of predicted sound speed values obtained using an example algorithm as described in this specification vs. observed experimental results.

A similar linear multi-regression analysis was performed for fluid sound speed sensitivity. The results of the multi-regression analyses for fluid sound speed identification are shown in Table 3 and FIG. 12 for a range of fluid properties associated with sixty four (64) different density/sound-speed combinations shown in Table 4.

TABLE 3

Max. Error = 25.66 m/sec
Avg. Error = 7.91 m/sec
Sound_Speed R^2 = 0.99789

| ss_function | ss_coeff | t_test | p_test |
|---|---|---|---|
| "DPH" | 1.836454704148E+00 | 4.053817323E+02 | 1.859732235E−110 |
| "(DR − DPHBW)" | −2.048583785107E+00 | −4.435181755E+02 | 5.906131186E−113 |
| "(DI2 − DPHBW)^(1/2)" | 2.770669897048E+01 | 5.998499382E+03 | 2.417310378E−185 |

$$ss = \alpha_1 DPH + \alpha_2(DR - DPHBW) + \alpha_3\sqrt{DI2 - DPHBW}$$

TABLE 4

| Density (g/cc) | Sound Speed (m/s) | Predict Sound speed (m/s) | Error (m/s) |
| --- | --- | --- | --- |
| 0.01278 | 323.2 | 323.2 | 0 |
| 1 | 900 | 909.57 | 9.57 |
| 1 | 930 | 939.01 | 9.01 |
| 1 | 960 | 968.36 | 8.36 |
| 1 | 990 | 997.63 | 7.63 |
| 1 | 1020 | 1026.82 | 6.82 |
| 1 | 1050 | 1055.93 | 5.93 |
| 1 | 1080 | 1084.95 | 4.95 |
| 1 | 1110 | 1113.88 | 3.88 |
| 1 | 1140 | 1142.73 | 2.73 |
| 1 | 1170 | 1171.48 | 1.48 |
| 1 | 1200 | 1200.15 | 0.15 |
| 1 | 1230 | 1228.72 | 1.28 |
| 1 | 1260 | 1257.19 | 2.81 |
| 1 | 1290 | 1285.57 | 4.43 |
| 1 | 1320 | 1313.86 | 6.14 |
| 1 | 1350 | 1342.04 | 7.96 |
| 1 | 1380 | 1370.13 | 9.87 |
| 1 | 1410 | 1398.11 | 11.89 |
| 1 | 1440 | 1425.99 | 14.01 |
| 1 | 1470 | 1453.76 | 16.24 |
| 1 | 1500 | 1481.42 | 18.58 |
| 0.8 | 900 | 910.2 | 10.2 |
| 0.8 | 930 | 939.88 | 9.88 |
| 0.8 | 960 | 969.5 | 9.5 |
| 0.8 | 990 | 999.05 | 9.05 |
| 0.8 | 1020 | 1028.55 | 8.55 |
| 0.8 | 1050 | 1057.98 | 7.98 |
| 0.8 | 1080 | 1087.34 | 7.34 |
| 0.8 | 1110 | 1116.64 | 6.64 |
| 0.8 | 1140 | 1145.87 | 5.87 |
| 0.8 | 1170 | 1175.04 | 5.04 |
| 0.8 | 1200 | 1204.14 | 4.14 |
| 0.8 | 1230 | 1233.17 | 3.17 |
| 0.8 | 1260 | 1262.12 | 2.12 |
| 0.8 | 1290 | 1291.01 | 1.01 |
| 0.8 | 1320 | 1319.82 | 0.18 |
| 0.8 | 1350 | 1348.56 | 1.44 |
| 0.8 | 1380 | 1377.23 | 2.77 |
| 0.8 | 1410 | 1405.82 | 4.18 |
| 0.8 | 1440 | 1434.33 | 5.67 |
| 0.8 | 1470 | 1462.77 | 7.23 |
| 0.8 | 1500 | 1491.12 | 8.88 |
| 0.6 | 900 | 874.34 | 25.66 |
| 0.6 | 930 | 907.42 | 22.58 |
| 0.6 | 960 | 940.4 | 19.6 |
| 0.6 | 990 | 973.29 | 16.71 |
| 0.6 | 1020 | 1006.09 | 13.91 |
| 0.6 | 1050 | 1038.78 | 11.22 |
| 0.6 | 1080 | 1071.38 | 8.62 |
| 0.6 | 1110 | 1103.87 | 6.13 |
| 0.6 | 1140 | 1136.26 | 3.74 |
| 0.6 | 1170 | 1168.54 | 1.46 |
| 0.6 | 1200 | 1200.71 | 0.71 |
| 0.6 | 1230 | 1232.77 | 2.77 |
| 0.6 | 1260 | 1264.73 | 4.73 |
| 0.6 | 1290 | 1296.56 | 6.56 |
| 0.6 | 1320 | 1328.28 | 8.28 |
| 0.6 | 1350 | 1359.88 | 9.88 |
| 0.6 | 1380 | 1391.36 | 11.36 |
| 0.6 | 1410 | 1422.71 | 12.71 |
| 0.6 | 1440 | 1453.94 | 13.94 |
| 0.6 | 1470 | 1485.04 | 15.04 |
| 0.6 | 1500 | 1516.01 | 16.01 |

The maximum value of the 'p-test' coefficients is p_test<<0.05, which indicates that the calculated model is highly relevant to the underlying physics and not simply a numerical artifact of the data set. This linear model is also based on three parametric functions involving resonance frequency shifts as well as distortion due to change in the resonance bandwidth:

$$ss = \alpha_1 DPH + \alpha_2 (DR - DPHBW) + \alpha_3 \sqrt{DI2DPHBW}$$

The maximum calculated sound speed error over the range of sixty four fluid properties sets was 25.66 m/sec, or 2.93%.

The technologies described in this specification may be further adapted to estimate multiphase properties of fluids, for example, gas/oil ratio (GOR), fraction of brine in oil, or the density of an oil portion of a multiphase fluid.

All or part of the technologies described in this specification and their various modifications can be implemented or controlled, at least in part, via a computer program product, such as a computer program tangibly embodied in one or more information carriers, such as in one or more tangible machine-readable storage media, for execution by, or to control the operation of, data processing apparatus, such as a programmable processor, a computer, or multiple computers.

A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with operating or controlling the tools can be performed or controlled by one or more programmable processors executing one or more computer programs to perform the functions of the calibration process. All or part of the tools can be controlled using special purpose logic circuitry, for example, an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, for example, magnetic, magneto-optical disks, or optical disks. Non-transitory machine-readable storage media suitable for embodying computer program instructions and data include all forms of non-volatile storage area, including by way of example, semiconductor storage area devices such as EPROM, EEPROM, and flash storage area devices; magnetic disks such as internal hard disks or removable disks; magneto-optical disks; and CD-ROM and DVD-ROM disks.

Each computing device, such as server, may include a hard drive for storing data and computer programs, and a processing device (for example, a microprocessor) and memory (for example, RAM) for executing computer programs.

Elements of different implementations described in this specification may be combined to form other implementations not specifically set forth above. Elements may be left out of the tools and associated components described in this specification without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. An apparatus for fluid measurement, the apparatus comprising:
   a leaf cell sensor having one or more piezoelectric radial components connected to a circumferential component, the one or more radial components and the circumferential component having a distal face and a proximal face;
   a first electrode positioned on the distal face of at least one radial component;
   a second electrode positioned on the proximal face of the at least one radial component;
   a voltage source having a negative terminal and a positive terminal, the negative terminal being connected to the first electrode and the positive terminal being connected to the second electrode;
   an electric current measurement device connected to the first and second electrode to measure current flowing between the first and second electrode; and
   a processor of a computing device and a non-transitory computer readable medium storing instructions thereon, wherein the instructions, when executed, cause the processor to determine, from the measured current, one or more properties of the fluid comprising fluid density,
   where fluid density (rho) is determined at least in part based on the equation $$rho = \alpha_1(DR-DPHBW) + \alpha_2(DI2-DPHBW) + \alpha_3\sqrt{DM2}$$

where DR denotes a peak shift in a real part of complex admittance between air and fluid, DPHBW denotes change in bandwidth between air and fluid, DI2 denotes the valley shift in the imaginary part of admittance between air and fluid, DM2 denotes the valley shift in admittance magnitude between air and fluid, and $\alpha_1$, $\alpha_2$, $\alpha_3$ denote regression coefficients.

2. The apparatus of claim 1, where the circumferential component has a shape based on contour segments of the canonical Rhodonea conformal mapping geometry.

3. The apparatus of claim 1, where the one or more properties of the fluid further comprise fluid sound speed.

4. The apparatus of claim 1, where determining comprises determining electrical admittance spectra.

5. The apparatus of claim 3,
   where fluid sound speed (SS) is determined at least in part based on the equation $$ss = \alpha_1 DPH + \alpha_2(DR-DPHBW) + \alpha_3\sqrt{DI2DPHBW}$$

where DPH denotes a difference in phase peak of admittance between air and fluid, DR denotes a peak shift in the real part of admittance between air and fluid DPHBW denotes change in bandwidth between air and fluid, DI2 denotes the valley shift in the imaginary part of admittance between air and fluid, and $\alpha_1$, $\alpha_2$, $\alpha_3$ denote regression coefficients.

6. An apparatus for fluid measurement, the apparatus comprising:
   a leaf cell sensor having one or more piezoelectric radial components connected to a circumferential component, the one or more radial components and the circumferential component having a distal face and a proximal face;
   a first electrode positioned on the distal face of at least one radial component;
   a second electrode positioned on the proximal face of the at least one radial component; and
   a voltage source having a negative terminal and a positive terminal, the negative terminal being connected to the first electrode and the positive terminal being connected to the second electrode,
   where the leaf cell sensor comprises eight radial components.

7. The apparatus of claim 1, where the leaf cell sensor comprises lead zirconate titanate.

8. The apparatus of claim 1, where the circumferential component has an outer diameter of between 8 mm and 12 mm.

9. The apparatus of claim 1, where the apparatus is integrated into a production logging tool or a logging while drilling tool.

10. A method for measuring one or more properties of a fluid, the method comprising:
    immersing the apparatus of claim 1 into a volume of the fluid;
    applying a sinusoidal voltage across the first electrode and the second electrode, thereby inducing a sinusoidal strain in the piezoelectric radial component;
    measuring a current flowing between the first electrode and the second electrode; and
    determining, from the current, the one or more properties of the fluid comprising fluid sound speed,
    where fluid sound speed (SS) is determined at least in part based on the equation $$ss = \alpha_1 DPH + \alpha_2(DR-DPHBW) + \alpha_3\sqrt{DI2DPHBW}$$

where DPH denotes a difference in phase peak of admittance between air and fluid, DR denotes a peak shift in the real part of admittance between air and fluid, DPHBW denotes change in bandwidth between air and fluid, DI2 denotes the valley shift in the imaginary part of admittance between air and fluid, and $\alpha_1$, $\alpha_2$, $\alpha_3$ denote regression coefficients.

11. The method of claim 10, where the one or more properties of the fluid further comprise fluid density.

12. The method of claim 10, where the determining step comprises determining electrical admittance spectra.

13. The method of claim 10, comprising one or more reference measurements in air.

14. The method of claim 11,
    where fluid density (rho) is determined at least in part based on the equation $$rho = \alpha_1(DR-DPHBW) + \alpha_2(DI2-DPHBW) + \alpha_3\sqrt{DM2}$$

where DR denotes a peak shift in a real part of complex admittance between air and fluid, DPHBW denotes change in bandwidth between air and fluid, DI2 denotes the valley shift in the imaginary part of admittance between air and fluid, DM2 denotes the valley shift in admittance magnitude between air and fluid, and $\alpha_1$, $\alpha_2$, $\alpha_3$ denote regression coefficients.

15. The method of claim 13, where the fluid is a multiphase fluid.

16. The method of claim 13, where the fluid is a wellbore fluid.

* * * * *